United States Patent [19]

Honda et al.

[11] Patent Number: 5,290,927
[45] Date of Patent: Mar. 1, 1994

[54] PROCESS FOR PREPARING 2′,3′-DIDEOXYADENOSINE

[75] Inventors: Yutaka Honda; Hiroshi Shiragami; Hisao Iwagami; Masayuki Arai, all of Kawasaki, Japan

[73] Assignee: Ajinomoto Co., Inc., Tokyo, Japan

[21] Appl. No.: 317,567

[22] Filed: Mar. 1, 1989

[30] Foreign Application Priority Data

| Mar. 1, 1988 [JP] | Japan | 63-48425 |
| Jul. 11, 1988 [JP] | Japan | 63-170963 |
| Dec. 9, 1988 [JP] | Japan | 63-310131 |
| Dec. 19, 1988 [JP] | Japan | 63-320046 |

[51] Int. Cl.$^5$ ................ C07H 19/173; C07H 19/073
[52] U.S. Cl. ................................. 536/27.6; 536/55.3
[58] Field of Search .................... 536/23, 24, 26, 27.6

[56] References Cited

U.S. PATENT DOCUMENTS

| 4,564,612 | 1/1986 | Sugihara et al. | 514/211 |
| 4,892,865 | 1/1990 | Townsend et al. | 514/43 |
| 4,900,828 | 2/1990 | Belica et al. | 544/317 |

OTHER PUBLICATIONS

House et al. J. Amer. Chem. Soc. 80:182–187 (1958).
Jain et al. J. Org. Chem. 38(18):3179–3186 (1973).
March, Jerry, (1977) *Advanced Organic Chemistry: Reactions, Mechanisms and Structure* (McGraw-Hill: New York), pp. 944–945.
Robins et al. (1977) Can. J. Chem. vol. 55, pp. 1251–1259.
Robins et al. (1984) Tetrahedron Letters, vol. 25, No. 4, pp. 367–370.
*Fieser and Fieser*, Reagents for Organic Synthesis, pp. 1292–1293 (1967).

*Primary Examiner*—Johnnie R. Brown
*Assistant Examiner*—Gary L. Kunz
*Attorney, Agent, or Firm*—Oblon, Spivak, McClelland, Maier & Neustadt

[57] ABSTRACT

A process for preparing 2′,3′-dideoxyadenosine of the formula

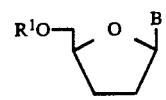

wherein B is adenine, wherein $R^1$ is hydrogen, $C_{1-12}$ acyl, $C_{1-12}$ alkyl, $C_{7-8}$ aralkyl, or silyl, said process comprising:
reducing a nucleoside of the formula IIIa or IIIb

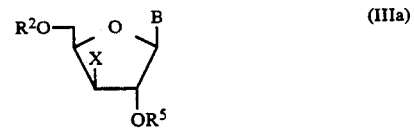

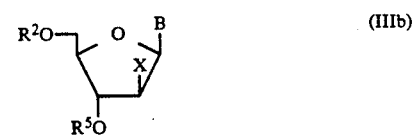

wherein $R^2$ is hydrogen, $C_{1-12}$ acyl, $C_{1-12}$ alkyl, $C_{7-8}$ aralkyl or silyl; X is Cl, Br or I; $R^5$ is $C_{1-12}$ acyl and B is adenine, with hydrogen in the presence of a palladium catalyst and aqueous solvent mixture of acetonitrile or ethyl acetate and water, said aqueous solvent containing a base selected from the group consisting of sodium hydroxide/sodium acetate and sodium carbonate/sodium acetate, wherein said solvent has a pH of 9–11.

12 Claims, No Drawings

PROCESS FOR PREPARING 2',3'-DIDEOXYADENOSINE

BACKGROUND OF THE INVENTION

1. Field of the Invention

The invention generally relates to processes for producing nucleoside derivatives.

2. Discussion of the Background

Dideoxynucleosides are expected to be useful in the field of medicaments because of their antiviral activity. Dideoxynucleosides are known compounds (for example, cf., H. Mitsuya and S. Broder, *Proc. Natl. Acad. Soc. USA*, vol. 93, 1911, 1986). Notably, 2',3'-dideoxyinosine, with its antiviral activity, is expected to serve as an effective medicine.

2',3'-Didehydro-2',3'-dideoxy-5'-O-acylinosines are important intermediates for the synthesis of various compounds having pharmaceutical activity.

The following documents disclose synthetic methods available for making 2',3'-dideoxynucleosides from nucleoside starting materials:

(1) M. J. Robins et al, *Tetrahedron Lett.*, 25, 367 (1984);

(2) B. Samuelsson et al, *Acta Chem. Scand*, B36, 251 (1982); and (3) J. Chattopadhyaya et al, *Acta Chem. Scand.*, B40, 251 (1982).

The methods disclosed by these documents however employ adenosine or protected adenosine as the base material.

No method has yet been reported for producing 2',3'-dideoxynucleosides from inosine. The main reason appears to be that no methods for the efficient removal of the zinc complex generated during such a process and which acts as a catalyst poison in the step of catalytic reduction are available.

In addition, 2',3'-didehydro-2',3'-dideoxyinosine derivatives tend to decompose during catalytic reduction when a hydrous solvent is used as the reaction medium, and no method is available to prevent this decomposition.

2',3'-Dideoxynucleosides of formula (B):

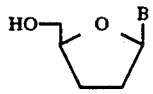

(B)

also have antiviral activity making them utilizable as drugs for treatment of, e.g., AIDS, etc. They can be used as medicaments (cf., Japanese Laid-Open Unexamined Patent Application No. 280500/1986 and *J. Med. Chem.*, 30 440 (1987)). In formula (B), B represents a base known in nucleic acid chemistry such as a purine base bound to the sugar via its 9-position, a pyrimidine base bound to the sugar via its 1-position, etc.

A method for the production of 2',3'-dideoxynucleosides is known in which the compound:

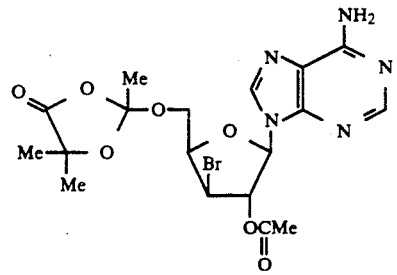

is reduced with hydrogen (H$_2$) using a palladium catalyst in the presence of triethylamine. The protective group is then removed to obtain the following 2',3'-dideoxyadenosine:

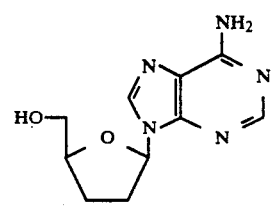

(cf., J. Am. Chem. Soc., 95, 4025 (1973)).

According to this method, the following 3'-deoxyadenosine:

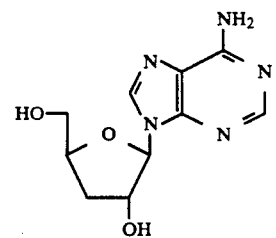

is produced in large quantities as an undesirable by-product, with formation ratios of the 2',3'-dideoxyadenosine to the 3'-deoxyadenosine reaching even 40:46. This method is consequently hardly advantageous from an industrial standpoint. Thus, a method for efficiently and selectively obtaining 2',3'-dideoxynucleosides using readily accessible starting materials at low cost is needed.

Some methods for preparing nucleoside derivatives, such as dideoxynucleosides, etc., using nucleosides as raw materials are known. Notably, nucleoside derivatives which are substituted at their 2'-position and 3'-position (or at their 3'-position and 2'-position thereof) by an acyloxy group and a halogen atom are important intermediates for preparing various substances showing pharmacological activities.

Compounds of formula (C) or formula (D) are important intermediates in these preparations:

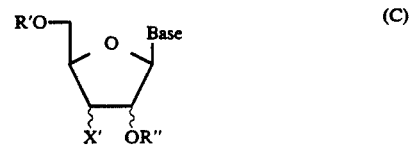

(C)

-continued

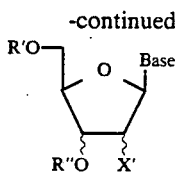

wherein:
Base is a purine base or a pyrimidine base;
X' is Cl, Br, or I;
R' is H or a protective group which is readily removed; and
R" is an acyl group.

The compounds of formula (C) and formula (D) can be transformed into dideoxynucleosides by a known method which comprises reducing the compounds with hydrogen over a Pd/C catalyst and then, if necessary, subjecting the product to hydrolysis or ester exchange.

Known methods for preparing compounds of formula (C) or formula (D) include the following:

(1) The method of John G. Moffatt et al which comprises reacting nucleosides with 2-acetoxyisobutyric acid bromide ((1) *J. Am. Chem. Soc.*, 95, 4025 (1973) (2) U.S. Pat. No. 3,658,787)). (2) The method of Morris J. Robbins et al which comprises reacting 2',3'-O-(1-methoxyethylidene)nucleoside with pivalic acid chloride in the presence of sodium iodide (*J. Am. Chem. Soc.*, 98, 8213 (1976)).

(3) The method of Engels et al which comprises reacting 2',3'-O-(1-ethoxyethylidene) adenosine derivatives with sodium iodide in the presence of a boron trifluoride-diethyl ether complex (*Tetrahedron Letters*, 21, 4339 (1980)).

(4) The method of John G. Moffatt et al which comprises reacting 2',3'-O-(1-ethoxyethylidene) adenosine with lithium bromide in acetonitrile, in the presence of a boron trifluoride-diethyl ether complex (*J. Org. Chem.*, 39, 30 (1974)).

(5) The method of Colin B. Reese et al which comprises reacting 2',3'-O-(1-ethoxyethylidene) adenosine with acetyl bromide in dichloroethane (*Synthesis*, 304, 1983).

Although the above-described methods for preparing the important intermediates of formulae (C) and (D) are known, they can not be used industrially because they suffer the following problems:

(1) the reaction proceeds in a high yield only when expensive reactants are used;
(2) many products are produced; and
(3) it is sometimes necessary to protect functional groups which do not take part in the reaction.

If any of these preparation methods were to be considered for the industrial production of nucleoside derivatives such as dideoxynucleosides, etc., these problems would all dramatically raise the cost of producing these materials.

In view of the growing importance of 2',3'-dideoxynucleosides in treating viral diseases, there is thus a distinct need for (an) efficient process(es) for producing these materials, and for (a) process(es) capable of efficiently providing intermediates used to make 2',3'-dideoxynucleosides.

SUMMARY OF THE INVENTION

Accordingly, it is an object of this invention to provide a novel process for the facile and efficient production of nucleoside derivatives.

It is another object of this invention to provide a novel process for producing 2',3'-dideoxynucleosides.

It is another object of this invention to provide a novel process for producing 2',3'-dideoxyinosine.

It is another object of this invention to provide a novel process for producing nucleoside derivatives from inosine.

It is another object of this invention to provide a novel process for producing 2',3'-didehydro-2',3'-dideoxy-5'-O-acyl inosine derivatives.

It is another object of this invention to provide a novel process for producing nucleoside intermediates and dideoxynucleosides having pharmacological activity, such as antiviral activity.

The process of the present invention which satisfies all of the above-noted objects of this invention and other objects which will become apparent from the description of the invention given herein below, may be outlined in general as follows.

Generally the process provides the transformation of a nucleoside of formula (I):

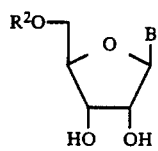

into a 2',3'-dideoxynucleoside of formula (A):

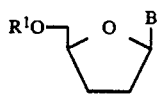

wherein B is a purine moiety, a pyrimidine moiety, an imidazole moiety, or a triazole moiety, and $R^1$ and $R^2$ are a hydrogen atom, a $C_{1-12}$ acyl group, a $C_{1-12}$ alkyl group, a $C_{7-8}$ aralkyl group, or a silyl group.

More specifically in this process, a nucleoside of formula (I):

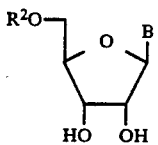

is transformed into a nucleoside derivative of formula (II):

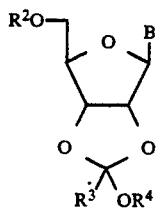

In the above formulae (III a and b) $R^3$ is H, $C_{1-5}$ alkyl or $C_{6-7}$ aryl, $R^4$ is $C_{1-12}$ alkoxy, $R^5$ is $C_{1-12}$ acyl,

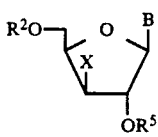 (IIIa)

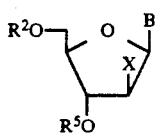 (IIIb)

which is then reduced to produce the 2′,3′-dideoxynucleoside of formula (A):

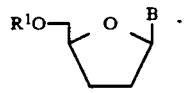

In the above formulae (III a and b) $R^3$ and $R^4$ are independently 1-($C_{1-12}$)-alkoxy-($C_{1-6}$)-alkyl or 1-($C_{1-12}$)-alkoxy-($C_{7-8}$)-arylalkyl, $R^5$ is $C_{1-12}$ acyl, and X is chlorine, bromine or iodine.

The reduction step may be carried out either (i) by treating the nucleoside derivative of formula (III a) or (III b) with hydrogen ($H_2$) over a palladium catalyst, or (ii) by treating the nucleoside derivative of formula (III a) or (III b) with a combination of zinc powder and acetic acid, or with a zinc copper reagent. Either of these treatments involving zinc is followed by a treatment with hydrogen in the presence of a palladium catalyst.

Thus the process of the present invention also permits producing a 2′,3′-didehydro-2′,3′-dideoxynucleoside derivative of formula (IV′):

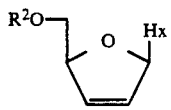

by reacting an inosine derivative of at least one of the formulae (III′ a and III′ b):

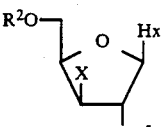 (III′a)

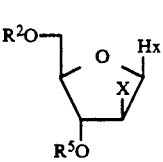 (III′b)

with a combination of zinc powder and acetic acid or with a zinc-copper reagent, followed by removal of the zinc complex.

The process of the present invention also permits making a nucleoside derivative by reacting a nucleoside which is 1-alkoxyalkylidenated or 1-alkoxyarylalkylidenated at the 2′-position and 3′-position with an acyl halide or with a combination of an organic acid anhydride and a hydrogen halide, in an organic solvent optionally containing an organic acid to introduce an acyloxy group and a halogen atom at the 2′-position and 3′-position (or the 3′-position and 2′-position of the nucleoside).

DETAILED DESCRIPTION OF THE PREFERRED EMBODIMENTS

In one of its embodiments, this invention provides new industrial processes for efficiently producing, from inosine, which is an inexpensive material, high-purity 2′,3′-didehydro-2′,3′-dideoxyinosine derivatives (compounds which are important intermediates for the synthesis of pharmaceutically active substances) and high-purity 2′,3′-dideoxyinosine (a compound having antiviral activity) in high yields.

With to the method of the present invention, 2′,3′-dideoxynucleosides can be prepared in a simple manner with high selectivity. With the present invention, the yield and purity of the nucleoside derivatives produced are dramatically improved over available processes, and the industrial production of these materials is very advantageous. Therefore, a variety of substances such as dideoxynucleosides, etc. showing pharmacological activities can be readily produced according to the present invention.

Another embodiment of this invention provides a process for efficiently removing the zinc complex in the reduction step, and also provides a process for the catalytic reduction of the product with little formation of hypoxanthine by-product.

The present invention thereby, in part, provides a new industrial process for efficiency producing, from inosine which is an inexpensive material, 2′,3′-didehydro-2′,3′-dideoxyinosine derivatives (compounds which are important intermediates for the synthesis of pharmaceutically active substances) and 2′,3′-dideoxyinosine (a compound having antiviral activity).

In this embodiment the inventors studied the application of conventional methods for producing 2′,3′-dideoxyadenosine from adenosine to a new method which uses inosine as the starting material. As a result of this study they discovered an industrially advantageous process for producing 2′,3′,-dideoxyinosine.

In this embodiment the invention provides a process for producing 2′,3′-didehydro-2′,3′-dideoxynucleoside derivatives represented by the following general formula (IV′):

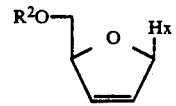

wherein $H_x$ is a hypoxanthine residue linked to the sugar molecule via its 9-position, and $R^2$ is a hydrogen atom or an easily removed known protective group.

This process relies on the reaction of an inosine derivative represented by at least one of the following general formulae (III′ a and b):

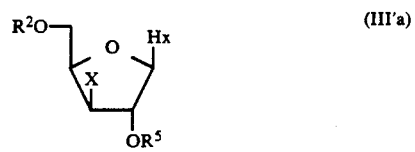 (III′a)

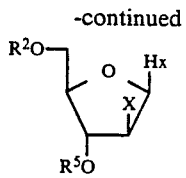

wherein $H_x$ and $R^2$ are as defined above; X is Cl, Br or I; and $R^5$ is a $C_{1-12}$ acyl group, with a zinc reagent (which may either be a combination of zinc powder and acetic acid, or a zinc-copper reagent) in an organic solvent, followed by removal of the zinc complex formed.

The zinc complex formed is removed by using an ion exchange resin, an adsorption resin or a chelate resin. The zinc complex form can also be removed by treatment of the reaction product with an organic solvent and water or with an organic solvent and an aqueous solution containing a chelating agent.

The chelating agent used may be ethylenediamine tetraacetic acid, oxalic acid, citric acid, glycolic acid, polyphosphoric acid, or a salt of one of these acids. The organic solvent may be chloroform, dichloroethane, acetonitrile, ethylacetate, or a mixture of these.

The 2',3'-didehydro-2',3'-dideoxynucleoside derivative (IV') thus obtained is then subjected to catalytic reduction by contacting derivative (IV') with hydrogen ($H_2$) in the presence of a palladium catalyst, followed by hydrolysis or ester exchange reaction, if needed, to provide a 2',3'-dideoxynucleoside derivative of the formula (A'):

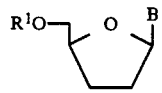

wherein $R^1$ is hydrogen, $C_{1-12}$ aryl, $C_{1-12}$ alkyl, $C_{7-8}$ aralkyl or silyl.

In accordance with the invention 2',3'-dideoxynucleoside derivatives (A') can be continuously produced from inosine on an industrial scale according to the reaction scheme set out below.

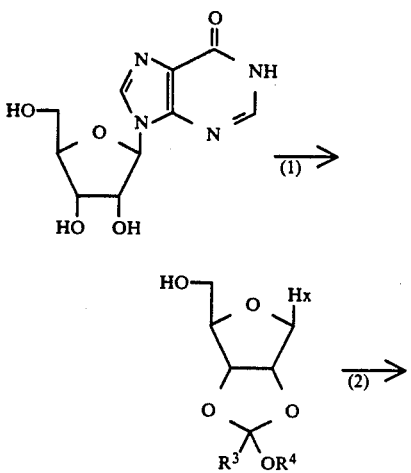

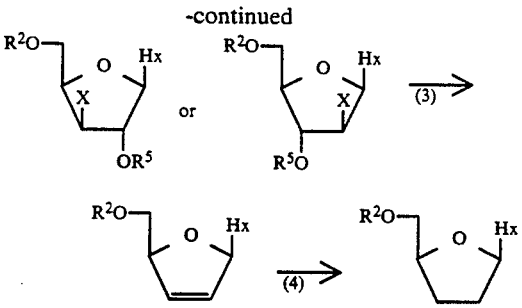

wherein $R^3$ is H, $C_{1-5}$ alkyl or $C_{6-7}$ aryl, $R^4$ is $C_{1-12}$ alkoxy; and $R^2$, $R^5$, $H_x$ and X are as defined above.

Step 1 is a modification of the method of *Mengel et al.* (*Liebig Anm. Chem.*, 1585 (1977), in which inosine is allowed to react with a tri-($C_{1-12}$)-alkyl ortho-($C_{1-8}$)-carboxylate in dimethyl-formamide (DMF) containing an organic acid. This gives an inosine derivative (II') in which the hydroxyl groups at 2'-and 3'-positions are substituted by a 1-alkoxyalkylidene or a 1-alkoxyarylalkylidene group.

Examples of the organic acid which may be used include trichloroacetic acid, p-toluenesulfonic acid and others. The carbon number of the alkoxy group in the 1-alkoxyalkylidene or 1-alkoxyarylalkylidene group is in the range from 1 to 12 (e.g., methoxy and ethoxy groups). The alkylidene group in the 1-alkoxyalkylidene group may contain 1 to 6 carbon atoms. For example, it may be methylidene or ethylidene. The arylalkylidene group in the 1-alkoxyarylakylidene group may contain 7 or 8 carbon atoms. For example, it may be benzylidene.

In Step 2, the inosine derivative (II') obtained is allowed to react in an organic solvent with a $C_{1-12}$ acyl halide, or with the combination of an organic acid anhydride (corresponding to the acyl halide) and a hydrogen halide, in the presence or absence of an organic acid. This gives an inosine derivative (III'a or III'b) having the corresponding acyloxy group and the corresponding halogen atom introduced at the 2'-and 3'-positions (or 3'- and 2'-positions) of the molecule, respectively.

The organic acid which may be used may have 1 to 12 carbon atoms (e.g., it may be formic, acetic or propionic acid).

The organic solvent which may be used includes acetonitrile, dioxane, trimethyl phosphate, dichloromethane or DMF.

The halogen atom in the acyl halide is chlorine, bromine or iodine, and the acyl group in the acyl halide may be an alkyl or an aralkyl group and may have 2 to 12 carbon atoms and 7 to 12 carbon atoms, respectively (e.g., acetyl and benzoyl).

The organic acid constituting the acid anhydride may have 2 to 12 carbon atoms (e.g., acetic and propionic acids). The most preferred anhydride is acetic anhydride.

As the hydrogen halide, one may use hydrogen chloride, hydrogen bromide or hydrogen iodide.

In Step 3, an inosine derivative (III'a or III'b) is allowed to react with zinc powder and acetic acid in an organic solvent. The zinc complex formed is then efficiently removed, giving the corresponding 2',3'-didehydro-2',3'-dideoxy-5'-O-acylinosine (IV') as a pure product.

The organic solvent used in this step may be methanol, ethanol, acetonitrile, THF, DMF, or a mixture thereof.

Removal of the zinc complex can be achieved by the use of an ion-exchange resin, an adsorption resin or a chelate resin, or by treatment with an organic solvent and water or an aqueous solution of a chelating agent. As examples of the chelating agent, there may be mentioned, among others, ethylenediaminetetraacetic acid, oxalic acid, citric acid, glycolic acid, polyphosphoric acid, and inorganic salts thereof. As the organic solvent, one may use chloroform, dichloromethane, acetonitrile, ethyl acetate and others.

In Step 4, inosine derivative (IV') is subjected to reduction with hydrogen ($H_2$) in an organic solvent over a palladium catalyst. This reduction proceeds with minimum substrate decomposition. This is followed by hydrolysis or ester exchange reaction, giving 2',3'-dideoxyinosine derivative (A').

Examples of the organic solvent one may use in the reduction include methanol, ethanol, isopropanol, acetonitrile and ethyl acetate.

As the Pd catalyst, one may use a Pd—carbon, a Pd—$BaCO_3$ or a Pd—$CaCO_3$ catalyst.

The introduction of the 1-alkoxyalkylidene or 1-alkoxyarylalkylidene group onto the hydroxyl groups of the inosine derivatives may be effectuated by using the known method of Mengel et al (*Liebig. Anm. Chem.*, 1585 (1977)). This method employs hydrogen chloride in DMF. This method, however, suffers problems when used in an industrial process. One of these is the necessity of using hydrogen chloride and anhydrous reaction conditions.

Intensive studies have led the inventors to discover that the use of an organic acid in DMF readily gives inosine derivatives (II') with the hydroxyl groups at the 2'- and 3'-positions of the molecule substituted by a 1-alkoxyalkylidene or a 1-alkoxyarylalkylidene group in high yields.

The organic acid used with the DMF should preferably be a carboxylic acid, such as trichloroacetic acid, or a sulfonic acid, such as p-toluenesulfonic acid. When trichloroacetic or p-toluenesulfonic acid is used as the catalyst, the reaction proceeds smoothly at a catalyst concentration of 10 mol% (relative to the substrate) or lower.

At the end of the reaction, the DMF is distilled-off under reduced pressure. Ethyl acetate is then added to the residue, followed by filtration, giving pure inosine derivatives (II') free of the organic acid.

The carbon number of the alkoxy group in the alkoxyalkylidene group is in the range from 1 to 12. Illustrative examples of the alkoxy group include methoxy, ethoxy, propoxy, butoxy, pentyloxy and hexyloxy. Of these, methoxy and ethoxy are preferred on the basis of cost.

As the alkylidene group in the alkoxyalkylidene group, methylidene and ethylidene are the most practical to use. Benzylidene is the most practical arylalkylidene group to use in the alkoxyarylalkylidene group.

The inosine derivative (II') thus obtained is then allowed to react in an organic solvent with an acyl halide, or with the combination of an organic acid anhydride and a hydrogen halide, in the presence of an organic acid, to give inosine derivative (III' a or III' b) with the corresponding acyloxy group and the corresponding halogen atom introduced to the 2'- and 3'-positions (or 3'- and 2'-positions), respectively.

Preferable examples of the organic solvent which may be used in this step include acetonitrile, dioxane and trimethyl phosphate. The organic acid used with the organic solvent may be any acid having 1 to 12 carbon atoms (e.g., acetic, propionic or butyric acid). The use of formic acid or acetic acid is preferred. The reaction readily proceeds even in the absence of an organic acid, but a longer time is needed to complete the reaction.

The halogen atom in the acyl halide reagent used may be chlorine, bromine or iodine. The acyl group in the acyl halide may have 2 to 12 carbon atoms (e.g., acetyl, propionyl, oxalyl, malonyl, benzoyl or toluoyl). Of these, acetyl and benzoyl groups are preferred.

As the organic acid anhydride (second reagent), one may use acetic, propionic or butyric anhydrides. Of these, acetic anhydride is preferred in terms of availability and reaction efficiency.

The hydrogen halide (third reagent) is hydrogen chloride, bromide or iodide, which may be added in the form of gas or may be generated in situ.

The amount of acyl halide (or organic acid anhydride and hydrogen halide) used may be in the range of 1 to 5 equivalents (most preferably 3 to 4 equivalents) of the weight of inosine derivative (II') used.

The reaction is allowed to proceed at a temperature in the range from 0° to 75° C., preferably in the range from 0° to 20° C.

The reaction time varies with reaction temperature, but it is preferably in the range from 0.5 to 3.0 hours at a temperature in the range of 15° to 20° C.

The steps of producing 2',3'-didehydro-2',3'-dideoxy-5'-O-acylinosine derivative (IV') by reaction of inosine derivative (III' a or III' b) with zinc powder in an organic solvent in the presence of acetic acid and the method of removing the zinc complex formed is explained below. The zinc complex, if left unremoved, significantly retards the catalytic reduction in the succeeding step, and forms zinc hydroxide gel when treated with water, making purification of the product extremely difficult. Hence, efficient removal of zinc complex is indispensable for obtaining a pure product in a high yield.

As the organic solvent for the reaction in this step, one may use methanol, ethanol, acetonitrile, tetrahydrofuran (THF), dimethylformamide (DMF) and others. A zinc-copper reagent may be used in place of the combination of zinc powder and acetic acid. The preferable amounts of zinc powder and acetic acid used are both 2 to 3 equivalents of the weight of substrate used, and the reaction is completed in 15 to 120 minutes at room temperature. A corresponding amount of zinc-copper reagent is used.

At the end of the reaction, the organic solvent is distilled-off. The residue obtained may be purified by any one of the methods described below.

One such method involves dissolving the residue in aqueous ammonia, and to treat this solution with an adsorption resin (e.g., SP-207 available from Mitsubishi Chemical Industries), followed by elution with a mixture of aqueous ammonia and methanol. This method can also be applied to the purification of 2',3'-didehydro-2',3'-dideoxyinosine (with the 5'-acyl group being eliminated).

A second method involves dissolving the residue in methanol, and treating this solution with a chelate resin (e.g., CR-10 available from Mitsubishi Chemical Industries), followed by elution with methanol. This method may also be carried out in a batch process.

A simpler method is the treatment of the reaction mixture with an organic solvent (such as chloroform or dichloromethane) and water, which water may contain a chelating agent. The preferable combination is the use of a solvent (acetonitrile, THF, or ethyl acetate) and an aqueous solution of a chelating agent. The zinc complex is thus completely transferred to the aqueous layer, and pure 2',3'-didehydro-2',3'-dideoxyinosine (IV') is quantitatively recovered from the organic layer. An aqueous solution of EDTA-2Na (an exemplary chelating agent) is preferably prepared from EDTA and sodium hydroxide immediately before use and used under neutral or acidic conditions.

The 2',3'-didehydro-2',3'-dideoxy-5'-O-acylinosine (IV') thus obtained is then subjected to catalytic reduction to give 2',3'-dideoxyinosine (A') in the next step. Since the starting material (IV') and the reaction product (A') in the reduction step are both very unstable towards acids, the reaction system must be maintained under neutral or alkaline pH conditions throughout the entire course of reaction (i.e. pH≧7).

In addition, it must be noted that water, if contained in the reaction medium, greatly accelerates the decomposition of substrate during catalytic reduction. It is therefore preferable to use, as the reaction medium, a non-aqueous solvent such as methanol, ethanol, isopropanol, acetonitrile or ethyl acetate.

Suitable palladium catalysts which may be used in this reduction include Pd—carbon, as well as Pd—BaCO$_3$ and Pd—CaCO$_3$ which are generally considered to be less active for the hydrogenation of double bonds. It has also been discovered that the latter type of catalysts cause less contamination of the reaction system with moisture. Furthermore, Pd—BaCO$_3$ and Pd—CaCO$_3$ are more suitable for industrial production because they do not present the danger of ignition.

The reaction rate varies with catalyst activity. When the catalyst is used in an amount of 5 to 30 mol% (as Pd) based on the weight of substrate (III'a or III'b), the reaction is completed in 1 to 6 hours at room temperature.

Table 1 lists the amounts of by-product hypoxanthine formed by this reaction when different types of Pd catalysts are used in the presence and in the absence of water. The result obtained shows that anhydrous conditions prevent the formation of hypoxanthine.

The reaction was carried out using 15.0 mg of pure 2',3'-didehydro-2',3'-dideoxy-5'-O-acetylinosine dissolved in 2 ml ethanol. The reaction mixture was analyzed by liquid chromatography to measure the amounts of the starting material (IV'), the reaction product 2',3'-dideoxyinosine (A'), and the by-product, hypoxanthine (H$_x$).

TABLE 1

| Catalyst | Weight (mg) | Area ratio in liquid chromatogram | | | Reaction Time (hr) |
|---|---|---|---|---|---|
| | | (III) | (IV) | (H$_x$) | |
| 2% Pd—C (wet) | 50 | 5 | 62 | 33 | 3.0 |
| 10% Pd—C (wet) | 15 | 3 | 63 | 34 | 4.0 |
| 5% Pd—C | 15 | 0 | 88 | 12 | 6.0 |
| 5% Pd—CaCO$_3$ | 25 | 0 | 85 | 15 | 6.0 |
| 5% Pd—BaCO$_3$ | 40 | 4 | 85 | 11 | 6.0 |
| 30% Pd—BaCO$_3$ | 15 | 0 | 91 | 9 | 1.5 |
| 5% Pd—BaSO$_4$ | 15 | 73 | 22 | 5 | 12.5 |
| 30% Pd—BaCO$_3$ (with 200 μl H$_2$O added) | 15 | 0 | 82 | 18 | 3.5 |
| 30% Pd—BaCO$_3$ (with 400 μl H$_2$O added) | 15 | 0 | 78 | 22 | 2.0 |

TABLE 1-continued

| Catalyst | Weight (mg) | Area ratio in liquid chromatogram | | | Reaction Time (hr) |
|---|---|---|---|---|---|
| | | (III) | (IV) | (H$_x$) | |

Note
1) Pd—C (wet): Contains about 5% water based on the total weight of catalyst
2) Liquid chromatography conditions:
Column: YMC-Pack A 312 ODS (6 φ mm × 150 mm; Yamamura Kagaku-kenkyu-sho)
Eluent: 20% acetonitrile
Elution rate: 1.6 ml/min, Detection wavelength: 260 nm In another embodiment, the inventors have found that by converting a compound of formula (X):

into at least one compound of formula (III a or III b):

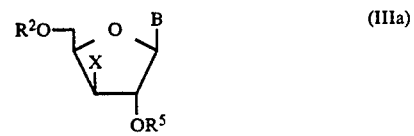

(IIIa)

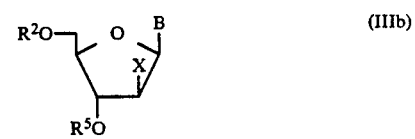

(IIIb)

and then reducing the compound of formula (III a) or (III b) with hydrogen (H$_2$) in a solvent mixture of an organic solvent and water over a palladium catalyst using a base, the 2',3'-dideoxynucleoside of formula (A):

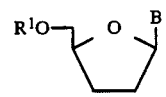

is selectively obtained in a high yield, and the yield of undesired compounds of formulae (E) and (F):

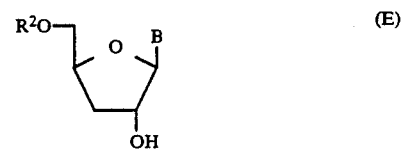

(E)

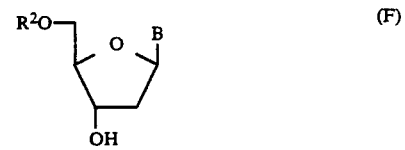

(F)

is markedly prevented.

In the formulae described above, R$^5$ represents a hydrogen atom or an acyl group having 1 to 12 carbon atoms, R$^2$ represents a hydrogen atom, an acyl group having 1 to 12 carbon atoms, an alkyl group having 1 to 2 carbon atoms, an aralkyl group having 7 to 12 carbon atoms or a silyl group; X represents a halogen atom; and B represents a purine base bound to a sugar residue, via its 9-position, a pyrimidine base bound via its 1-position, an imidazole base bound via its 1-position or a triazole base bound via its 1-position.

Examples of the acyl group for $R^5$ include an acetyl group, a propionyl group, a benzoyl group, etc. Examples of the acyl group for $R^2$ include an acetyl group, a propionyl group, a benzoyl group, etc. Examples of the alkyl group include a methyl group, an ethyl group, a propyl group, etc. Examples of the aralkyl group include a benzyl group, a phenylethyl group, a phenylpropyl group, etc. Examples of the halogen atom for X include chlorine, bromine, iodine, etc.

Examples of the purine base for B include adenosine, guanosine, hypoxanthine, xanthine, 6-chloropurine, 6-mercaptopurine, 6-methylthiopurine, 2,6-dichloropurine, 2-chloropurine, 2,6-diaminopurine, 2-amino-6-chloropurine, 2-aminopurine, etc. Examples of the pyrimidine base include uracil, cytosine, thymine, 5-fluorouracil, 5-chlorouracil, 5-bromouracil, 5-iodouracil, 5-ethyluracil, orotic acid, etc. Examples of the imidazole base include 5-amino-4-imidazole carboxamido, etc. And examples of the triazole base include 1,2,4-triazole-3-carboxamido, etc.. If necessary, the amino group, etc. in the base moiety may be protected.

Compounds of formulae (III a) and (III b) described above can be prepared from a compound of formula (I) described above in a conventional manner (cf., *J. Am. Chem. Soc.*, 95, 4025 (1973)).

The palladium catalyst used is not particularly limited, but it preferred that it be 1 to 10% palladium onto carbon which is either dried or contains water. It is preferred that an amount of the palladium catalyst used be approximately 1 to 10% in a molar ratio based on the compound of formula (III a) or (III b).

As the solvent, a solvent mixture of an organic solvent and water is preferred. Examples of the organic solvent include esters such as ethyl acetate, propyl acetate, etc.; hydrocarbons such as hexane, heptane, benzene, toluene, etc.; ethers such as dioxane, diethyl ether, tetrahydrofuran, etc.; halogenated hydrocarbons such as chloroform, dichloromethane, etc.; alcohols such as methanol, ethanol, isopropyl alcohol, etc.; ketones such as acetone, methyl, ethyl ketone, etc.; nitriles such as acetonitrile, propionitrile, etc. Among them, acetonitrile is particularly preferred. A ratio of organic solvent and water of from about 1 to about 10 may be used.

It is appropriate that the concentration of the compound of formula (III a) or (III b) dissolved in the solvent be approximately 1 to 20 wt.%.

High purity compounds of formula (A) can be obtained by subjecting a compound of formula (III a) or (III b) mentioned above to catalytic reduction in the presence of a palladium catalyst in a mixture of an organic solvent and water containing a base.

Examples of the base which may be used include organic bases (such as triethylamine, tripropylamine, tributylamine, pyridine, piperidine, or pyrrolidine), and inorganic bases. Of these, an inorganic base is preferably used.

Suitable inorganic bases include carbonates, bicarbonates, hydroxides, acetates, ammonia, and mixtures thereof. Illustrative examples of such bases include sodium carbonate, sodium acetate, sodium bicarbonate, sodium hydroxide, ammonium carbonate, and ammonium acetate. Of these, a mixture of sodium carbonate and sodium acetate is preferred.

The pH of the reaction system is maintained in the range from 9 to 11 by addition of a base mentioned above.

Results obtained by measuring the relationship of the reaction product and yield to the solvent and the base are shown in Table 2 below.

The compound of formula (III a) or (III b) used as the starting material was a compound in which $R^5$ is an acetyl group, $R^2$ is an acetyl group, X is bromine atom, and B is adenine.

TABLE 2

| Run No. | Solvent | Molar Ratio Based on (IIIa) or (IIIb) | Pd/(IIIa or b) mol % | Time (h) | (A) Yield (%) | (A)/[(E) + (F)] Formed Molar Ratio |
|---|---|---|---|---|---|---|
| 1 | MeCN—H$_2$O (10:1) | Na$_2$CO$_3$(1.1) AcONa(2.2) | 5 | 2 | 73.5 | 6.0 |
| 2[a] | MeCN—H$_2$O (10:1) | Na$_2$CO$_3$(1.1) AcONa(2.2) | 5 | 7 | 69.6 | 10.0 |
| 3 | MeCN—H$_2$O (10:1) | Na$_2$CO$_3$(1.1) | 5 | 2 | 69.4 | 4.3 |
| 4 | AcOEt—H$_2$O (5:1) | Na$_2$CO$_3$(3.1) | 5 | 3.5 | 67.3 | 3.6 |
| 5[b] | MeOH | Et$_3$N(1.4) | 10 | 3 | 60.5 | 2.4 |
| 6 | MeOH | Et$_3$N(22) | 10 | 1 | 50.7 | 1.4 |
| 7 | H$_2$O | Na$_2$CO$_3$(3.1) | 5 | 3 | 51.2 | 1.5 |

[a]The compound of formula (IIIa) or (IIIb) used as the raw material was an unpurified reaction mixture obtained from adenosine.
[b]Duplication of known method (J. Am. Chem., Soc., 95, 4025 (1973)).
MeCN: acetonitrile
H$_2$O: water
Na$_2$CO$_3$: sodium carbonate
AcONa: sodium acetate
AcOEt: ethyl acetate
MeOH: methanol
Et$_3$N: triethylamine The reaction product was analyzed by high performance liquid chromatography. As shown in Table 2 above, the mixture of water and organic solvent is preferred as the solvent.

As shown in Run Nos. 1 and 2 reported in Table 2, the formation ratio (A)/[(E)+(F)] shows a value as high as 6 to 10 when sodium carbonate and sodium acetate are used as the base in amounts of 1.1 and 2.2 molar proportions based on the compound (IIIa) or (IIIb). This is a level far higher in both yield and formation ratio compared with the data of Run No. 5 conducted according to the conventional method.

2′,3′-Dideoxynucleosides useful as antiviral agents, etc. are those wherein $R^2$ is generally a hydrogen atom. Therefore, in cases where $R^2$ is a protecting acyl group, etc., the protective group may be removed in a conventional manner after completion of the reduction step and subsequent purification of the product by chromatography or crystallization, etc. to obtain the desired compound.

In another embodiment, the present invention provides a novel method for producing nucleoside intermediates and dideoxynucleosides having pharmacological activities such as antiviral activity, etc. that is industrially practiceable.

The present inventors have duplicated the known methods to evaluate their reaction yields, relative difficulty in operations and production cost and then carried out further additional investigations. As a result, they have found a novel process which is superior to known processes.

That is, the present invention is directed to a process for the production of a nucleoside derivative which comprises reacting a nucleoside which is 1-alkoxyalkylidenated or 1-alkoxyarylalkylidenated at the 2'-position and 3'-position thereof with:

(1) an acyl halide; or (2) an organic acid anhydride and a hydrogen halide in an organic solvent containing an organic acid to introduce an acyloxy group and a halogen atom at the 2'-position and 3'-position thereof (or at the 3'-position and 2'-position thereof).

The organic acid contained in the organic solvent is an organic acid having 1 to 12 carbon atoms such as formic acid, acetic acid, propionic acid, etc.

The organic solvent which is used may be, for example, acetonitrile, dioxane, trimethyl phosphate, dichloromethane, etc.

The carbon atom number of the alkoxy group in the aforesaid 1-alkoxyalkylidenation or 1-alkoxyarylalkylidenation is 1 to 12. For example, methoxy or ethoxy group is adopted.

The alkylidene group in the 1-alkoxyalkylidene group is, for example, methylidene or ethylidene group. The arylalkylidene group in the 1-alkoxyarylalkylidene group is, for example, a benzylidene group.

The halogen atom in the acyl halide is, for example, chlorine, bromine or iodine.

The acyl group in the acyl halide is acetyl group or benzoyl, etc. and the carbon atom number is 2 to 12.

The organic acid constituting the organic acid anhydride is acetic acid, propionic acid, etc. and the carbon atom number 2 to 12. As the organic acid anhydride, acetic anhydride is preferred.

As the hydrogen halide, for example, hydrogen chloride, hydrogen bromide or hydrogen iodide may be used.

The nucleoside base is a purine base or a pyrimidine base. As the purine base, adenine, hypoxanthine, guanine, xanthine, etc. may be used. As the pyrimidine base, uracil, thymine, cytosine, etc. may be used.

The nucleoside derivative in which the acyloxy group and the halogen atom are introduced at the 2'-position and 3'-position (or at the 3'-position and 2'-position) of the molecule by the method of the present invention can be further subjected to, for example, hydrogenation and then to hydrolysis or ester exchange to deacyloxylate and dehalogenate the product, to obtain the dideoxynucleoside. The acyloxy group may be an acetoxy group, a benzyloxy group, etc. and the carbon atom number is approximately 2 to 12.

The nucleoside base is a purine base or a pyrimidine base. In this case, adenine, hypoxanthine, guanine, xanthine, etc. may be used.

As the starting material of the present invention, nucleosides obtained by subjecting ribonucleosides to 1-alkoxyalkylidenation or 1-alkoxyarylalkylidenation may be used. These alkylidenations may be performed in a conventional manner (for example, H. P. M. Fromageot et al, Tetrahedron, 23, 2315 (1967)). Further, in the ribonucleosides described above used to prepare the dideoxynucleosides, the base may be a purine base, or adenine, hypoxanthine, guanine, xanthine, etc.

The production of the nucleoside derivative in which the acyloxy group and the halogen atom are introduced at the 2'-position and 3'-position (or at the 3'-position and 2'-position) thereof, the organic acid used with the organic solvent may be formic acid, acetic acid, propionic acid, butyric acid, etc. as long as the carbon atom number of the organic acid is in a range of 1 to 12. Among these, the use of formic acid or acetic acid is preferred.

Further with respect to the organic solvent, acetonitrile, dioxane, trimethyl phosphate, etc. are preferred. Even though acid catalysts—for example, p-toluenesulfonic acid, methanesulfonic acid, trichloroacetic acid, etc.—used in the preparation of, e.g., 2',3'-O-(1-methoxyethylidene) adenosine, are present in the solution containing the solvent described above, the introduction of the acyloxy group and the halogen atom into the substrate is not affected at all.

Furthermore, the nucleosides which are 1-alkoxyalkylidenated or 1-alkoxyarylalkylidenated are known materials and can easily be prepared. In this case, the nucleosides are not particularly limited as long as the carbon atom number of the alkoxy group is in a range of 1 to 12. That is, mention may be made of methoxy, ethoxy, propoxy, butoxy, pentyloxy, hexyloxy, etc. Among them, methoxy and ethoxy are particularly preferred from a cost viewpoint. Further as the alkylidene group in the alkoxyalkylidene group, methylidene or ethylidene group is preferably used from a practical viewpoint. In addition, in the case of the arylalkylidene group, it is practical to use a benzylidene group.

Further the base constituting the nucleoside as the starting material may be any one of a purine base and a pyrimidine base. Of these, as the purine base, any of adenine, hypoxanthine, guanine and xanthine may be usable. As the pyrimidine base, uracil, thymine and cytosine are preferred.

As the halogen atom in the acyl halide which is used as one of the reactants, chlorine, bromine or iodine is usable. The acyl group in the acyl halide is not particularly limited as long as the carbon atom number is in a range of 2 to 12. For example, these may be acetyl, propionyl, oxalyl, malonyl, benzoyl, toluoyl, etc. Among them, an acetyl group and a benzoyl group are preferred.

As the organic acid anhydride which is likewise one of the reactants, acetic anhydride, propionic anhydride, butyric anhydride, etc. are usable. Among them, acetic anhydride which is readily accessible and provides a good reaction efficiency is preferred.

Further as the hydrogen halide reactant, any one of hydrogen chloride, hydrogen bromide and hydrogen iodide may be used. In this case, the hydrogen halide may be gaseous or may be prepared in the system.

The acyl halide or the organic acid anhydride and hydrogen halide used in the present invention are employed in a 1-fold to a 5-fold molar equivalent based on the 1-alkoxyalkylidenated or 1-alkoxyarylalkylidenated nucleoside which is the initial starting material. Preferably the amount is 3- to 4-molar equivalents.

The reaction temperature used at this stage is generally in a range of from 0° C. to 75° C., most preferably from 0° C. to 20° C. The reaction time may vary depending upon temperature but is preferably 0.5 to 3 hours at 15° to 20° C.

Under the foregoing conditions, the reaction described above is carried out using as the starting material the 1-alkoxyalkylidenated or 1-alkoxyarylalkylidenated nucleoside so that the nucleoside derivative having bound thereto the alkyloxy group and the halogen atom can be prepared in a high yield and high purity.

This embodiment will now be further described by the following illustrative non limiting specific example. A 2',3'-O-(1-methoxyethylidene) adenosine (formula (iii)) starting material was added to acetic acid containing acetyl bromide and the mixture was reacted to give a mixture composed mainly of the objective nucleoside derivative of formula (iv) and a compound of formula (v).

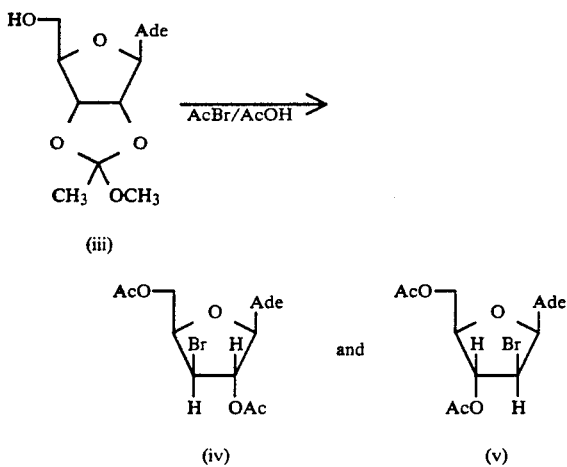

wherein Ade is adenine, and Ac is an acetyl group.

It must be noted that this reaction which uses acetic acid as the reaction solvent not only proceeds in a yield as high as 82% but also provides a product having a purity higher than that available in the prior art. The undesirable 2',3',5'-O-triacetyl adenosine by-product is only produced in an amount of below about 5%.

This method is extremely advantageous as an industrial process as compared to the Moffatt et al method noted above since the number of products are smaller.

Additionally, the major products of formula (iv) and formula (v) can be extracted with an organic solvent (for example, acetonitrile, ethyl acetate, etc.) without any loss of material. The extract is further advantageous in that it hardly contains hydrophilic impurities which cause a problem when the major products of formulae (iv) and (v) are converted into dideoxyadenosine (referred herein to as "DDA").

When 2',3'-O-(1-ethoxyethylidene) adenosine was reacted in acetic acid containing acetyl bromide, yields and purities similar to the specific example described above were obtained. However, according to the method of Reese et al (Synthesis, 304, 1983)—reaction conditions: heating under reflux for 15 minutes in dichloroethane—the yield and purity are both low and with this method it is difficult to control the reaction. Therefore, the advantages and novelty of the present invention are obvious. In addition, viewed from the standpoint of the prior art, it is surprising to be able to carry out the reaction of a nucleoside derivative in an acidic solvent such as acetic acid.

The present method for producing the deacyloxylated and dehalogenated dideoxynucleoside which is characterized by subjecting the nucleoside derivative in which an acyloxy group and a halogen group are introduced at the 2'-position and 3'-position (or at the 3'-position and 2'-position) to hydrogenation followed by hydrolysis or ester exchange may be illustrated as follows.

That is, after neutralizing the reaction solution described above with an inorganic base, the product is extracted with an organic solvent. As the base used in this case, a weak base such as an aqueous solution of sodium hydrogencarbonate, sodium carbonate, ammonia or the like, must be used. As the organic solvent for the extraction, acetonitrile, ethyl acetate, etc. can be used. The solvent of the product extract solution is distilled off under reduced pressure and the residue is dissolved in methanol. The solution is then subjected to hydrogenation in a flow of hydrogen in the presence of a Pd/C catalyst and triethylamine. After removal of the catalyst, a methanolic solution of sodium methoxide is added to the reaction solution to effect ester exchange, and the dideoxynucleoside is obtained.

As the base coponent of the nucleoside derivative used in the reaction described above, a purine base is preferred. Among the purine base, any one of adenine, hypoxanthine, guanine and xanthine may be sufficient.

Further as the starting material of the present invention, nucleosides obtained by subjecting ribonucleosides to 1-alkoxyalkylidenation or 1-alkoxyarylalkylidenation can be used. These alkylidenations may be performed according to the method of Fromageot et al as will be later described in the examples Further in the case of producing the dideoxynucleoside, the ribonucleoside described above preferably contains a purine base as constituent base and, adenine, hypoxanthine, guanine, xanthine, etc. are adopted.

Concretely, as will be later described in the examples, it has been found that the mixture of the compound of formula (iv) and the compound of formula (v) can be obtained in high yield by preparing 2',3'-O-(1-methoxyethylidene) adenosine from adenosine in a conventional manner and then either reacting the resulting adenosine derivative with acetyl bromide in an organic solvent containing acetic acid, or reacting with hydrogen bromide in acetic anhydride, without or after isolating the same.

In this case, the reaction solvent is a mixture system of acetic acid and the organic solvent used for preparing 2',3'-O-(1-methoxyethylidene) adenosine. If necessary, the compounds of formula (iv) and formula (v) are subjected to hydrogenation followed by hydrolysis of ester exchange by the known method, whereby DDA which is a dideoxynucleoside can be obtained.

The catalytic reduction is performed by treating the 2', 3'-didehydro-2',3'-dideoxynucleus derivative (IV') with hydrogen (H$_2$) in the presence of a palladium catalyst. The palladium catalyst may be a Pd-carbon, a Pd—BaCO$_3$ or a Pd—CaCO$_3$ catalyst. This reduction may be performed in an organic solvent. Suitable organic solvents which may be used include methanol, ethanol, isopropanol, acetonitrile or ethylacetate.

Other features of this invention will become apparent in the course of the following descriptions of exemplary embodiment which are given for illustration of the invention and that are now intended to be limiting thereof.

EXAMPLE 1

(1) To a suspension of 20.0 g (74.6 mmol) of inosine in 70 ml DMF, were added 14.2 ml (1.5 equivalent proportions, 111.8 mmol) trimethyl orthoacetate and 18.3 g (1.5 equivalent proportions, 111.8 mmol) trichloroacetate acid, and the mixture was stirred at room temperature for 12 hours. The reaction mixture was concentrated to about 20 ml, 150 ml ethyl acetate was added to the concentrate, and the resulting mixture was well stirred and filtered, giving 23.4 g (72.2 mmol, 96.8%) of 2',3'-O-(1-methoxyethylidene)inosine as a white powder. The structure of this product was supported by is NMR (300 MHz) and FAB-MS spectrum data.

(2) To a suspension of 10.0 g (37.3 mmol) of inosine in 25 ml DMF, were added 7.1 ml (1.5 equivalent proportions, 5.9 mmol) trimethyl orthoacetate and 710 mg (0.1 equivalent proportion, 3.7 mmol) p-toluenesulfonic acid monohydrate, and the mixture was stirred at room temperature for 12 hours. The reaction mixture was concentrated to about 10 ml, 100 ml ethyl acetate was added to the concentrate, and the resulting mixture was stirred well and filtered, giving 11.4 g (35.1 mmol, 94.0%) of 2',3'-O-(1-methoxyethylidene)-inosine as a solid.

EXAMPLE 2

To a suspension of 23.4 g (72.2 mmol) of 2',3'-O-(1-methoxyethylidene)inosine in 150 ml acetonitrile, was added dropwise 26.7 ml (5 equivalent proportions, 361 mmol) of acetyl bromide at room temperature over a period of 15 minutes, and the mixture was stirred at room temperature for five hours. The clear solution thus obtained was added dropwise to a suspension of 60.7 g (722 mmol) NaHCO$_3$ in 100 ml water over a period of 15 minutes, and the resulting mixture was extracted twice with 100 ml ethyl acetate. The extract was washed with saturated aqueous solution of sodium chloride and dried over anhydrous MgSO$_4$, and the dried solution was concentrated to dryness, giving 25.9 g (62.4 mmol, 86.4%) of faint yellow powder. Analysis by liquid chromatography showed that it is composed of 9-(2',5'-O-diacetyl-3'-bromo-3'-deoxy-$\beta$-D-xylofuranosyl)hypoxanthine and 9-(3',5'-O-diacetyl-2'-bromo-2'-deoxy-$\beta$-D-xylofuranosyl)hypoxanthine and further contains about 4% of 2',3',5'-triacetylinosine. The above structures were confirmed by recrystallizing the crude product from ethyl acetate and measuring the NMR (300 MHz) and FAB—MS spectrum data of the purified product.

EXAMPLE 3

The mixture of 9-(2',5'-O-diacetyl-3'-bromo-3'-deoxy-$\beta$-D-xylofuranosyl)hypoxanthine and 9-(3',5'-O-diacetyl-2'-bromo-2'-deoxy-$\beta$-D-xylofuranosyl)hypoxanthine obtained in Example 2 (8.50 g, 20.5 mmol) was suspended in a mixture of 25 ml acetonitrile and 25 ml methanol, 4.01 g zinc powder (3 equivalent proportions, 610.4 mml) and 2.58 ml acetic acid (2.2 equivalent proportions, 45.0 mmol) were added to this suspension, and the mixture was stirred at room temperature for one hour. Unreacted zinc powder was filtered off through Celite, 7.75 g (4.5 equivalent proportions, 92.3 mmol) NaHCO$_3$ was added to the filtrate, and the solvents were distilled off under reduced pressure. The residue was dissolved in 50 ml chloroform, 10 ml water was added and the mixture was stirred well. The organic layer was collected and dried over anhydrous MgSO$_4$, and the dried solution was concentrated.

The residue was purified by silica gel column chromatography (eluent: CHCL$_3$:MeOH=10:1 volume, 100 ml), giving 1.96 g (7.1 mmol, 34.7%) of pure 5'-O-acetyl-2',3'-didehydro-2',3'-dideoxyinosine as faint yellow powder. The structure of this product was supported by its NMR (300 MHz) and FAB—MS spectrum data.

EXAMPLE 4

5'-O-acetyl-2',3'-didehydro-2',3'-dideoxyinosine obtained in Example 3 (500 mg, 1.81 mmol) was suspended in 15 ml ethanol, 100 mg of 30% Pd—BaCO$_3$ was added to this suspension, and the mixture was stirred for two hours under a hydrogen gas stream. The catalyst was filtered off, the solvent was distilled off from the filtrate under reduced pressure, and the residue was analyzed by liquid chromatography, showing that it contained 445 mg (1.60 mmol, 88.4%) 5'-O-acetyl-2',3'-dideoxyinosine and 25 mg (0.18 mmol, 9.9%) hypoxanthine. The above structure was supported by the NMR (300 MHz) and FAB-MS spectrum data of purified product.

EXAMPLE 5

A mixture of 9-(2',5'-O-diacetyl-3'-bromo-3'-deoxy-$\beta$-D-xylofuranosyl)hypoxanthine and 9-(3',5'-O-diacetyl-2'-bromo-2'-deoxy-$\beta$-D-xylofuranosyl)hypoxanthine (1.0 g, 2.41 mmol) was suspended in a mixture of 5 ml acetonitrile and 5 ml methanol, 473 mg (3 equivalent proportions, 7.23 mmol) zinc powder and 0.30 ml (2.2 equivalent proportions, 5.30 mmol) acetic acid were added to this suspension, and the mixture was stirred at room temperature for one hour. Unreacted zinc powder was filtered off through Celite, 912 mg (4.5 equivalent proportions, 10.85 mmol) NaHCO$_3$ was added to the filtrate, and the solvents were distilled off under reduced pressure. Chloroform (40 ml) and water (3 ml) were added to the residue, and the mixture was stirred well and filtered. The organic layer was collected and dried over anhydrous MgSO$_4$, the dried solution was concentrated, and the residue was dissolved in 150 ml of a solvent mixture (CHCl$_3$:MeOH=10:1 by volume). The solution thus obtained was filtered through a 50-ml silica gel column, the filtrate was concentrated, 30 ml ethanol and 100 mg of 30% Pd—BaCO$_3$ were added to the residue, and the mixture was stirred for 12 hours under a hydrogen gas stream. After filtering off the catalyst, 2 ml of 2N—MaOH was added to the filtrate, and the mixture was stirred for 30 minutes. Analysis of the reaction mixture by liquid chromatography showed that it contained 255 mg (1.08 mmol, 44.8%) 2',3'-dideoxyinosine and 6.9 mg (0.05 mmol, 2.1%) hypoxanthine. The structure of this product was supported by the NMR (300 MHz) and FAB—MS spectrum data of isolated and purified product.

EXAMPLE 6

A mixture of 9-(2',5'-O-diacetyl-3'-bromo-3'-deoxy-$\beta$-D-xylofuranosyl)hypoxanthine and 9-(3',5'-O-diacetyl-2'-bromo-2'-deoxy-$\beta$-D-xylofuranosyl)hypoxanthine (1.5 g, 3.61 mmol) was allowed to react in the same 3, giving crude 5'-O-acetyl-2',3'-didehydro-2,'3'-dideoxyinosine. It was dissolved in 6 ml of 5% ammonia water, the solution was introduced to a 50-ml column packed with adsorption resin SP-207, and the column was washed with 1% ammonia water, followed by elution with 50% methanol. The eluate was concentrated to 50 ml, giving a mixture of 5'-O-acetyl-2',3'-didehydro-2',3'- dideoxyinosine and 2′,3′-didehydro-2′,3′-dideoxyinosine. It was mixed with 30 ml methanol, 250 mg of 10% Pd-carbon and 500 mg Na$_2$CO$_3$, and catalytic reduction was carried out under a hydrogen gas stream for four hours. After filtering off the catalyst, the filtrate was analyzed by liquid chromatography, showing the formation of 268 mg (1.13 mmol, 31.4%) 2′,3′-dideoxyinosine and 93 mg (0.68 mmol, 8.8%)hypoxanthine.

EXAMPLE 7

A mixture of 9-(2′,5′-O-diacetyl-3′-bromo-3′-diacetyl-2′-bromo-2′-deoxy-β-D -xylofuranosyl)hypoxanthine and 9-(3′,5′-O-diacetyl-2′-bromo-2′-deoxy-β-D-xylofuranosyl)hypoxanthine (200 mg, 0.48 mmol) was allowed to react in the same manner as in Example 3, giving crude 5′-O-acetyl-2′,3′-didehydro-2′,3′-dideoxyinosine.

It was mixed with 30 ml methanol and a small amount of acetic acid, 10 ml of chelate resin CR-10 was added to the resulting clear solution, and the mixture was stirred for five hours. After removing the resin by filtration, 50 mg of 30% Pd—BaCO$_3$ was added to the filtrate, and catalytic reduction was carried out under a hydrogen gas stream for seven hours. After filtering off the catalyst, 2 ml of 2N—NaOH was added to the filtrate, and the mixture was stirred for 30 minutes. The resulting reaction mixture was analyzed by liquid chromatography, showing the formation of 73 mg (0.31 mmol, 64.0%) 2′,3′-dideoxyinosine.

EXAMPLE 8

A mixture of 9-(2′,5′-O-acetyl-3′-bromo-3′-deoxy-β-D-xylofuranosyl)hypoxanthine and 9-(3′,5′-O-diacetyl-2′-bromo-2′-deoxy-β-D-xylofuranosyl)hypoxanthine (1.0 g, 2.4 mmol) was allowed to react in the same manner as in Example 3, giving crude 5′-0-acetyl-2′,3′-didehydro-2′,3′-dideoxyinosine. It was dissolved in a mixture of 30 ml acetonitrile and 15 ml ethyl acetate, and this solution was washed with 10 ml of an aqueous solution of EDTA-2Na (3 equivalent proportions, 7.23 mmol). The aqueous layer was extracted with a mixture of 10 ml acetonitrile and 5 ml ethyl acetate, the extract was washed with 5 ml of an aqueous solution of EDTA-2Na (1 equivalent proportion, 2.41 mmol), and the combined organic solution was concentrated to dryness. The residue was dissolved in 30 ml methanol, 200 mg of 30% Pd—CaCO$_3$ and 100 mg NaHCO$_3$ were added to the solution, and catalytic reduction was carried out under a hydrogen gas stream for six hours. After filtering off the catalyst, 4 ml of 2N—NaOH was added to the filtrate, and the mixture was stirred for 30 minutes and analyzed by liquid chromatography, showing the formation of 469 mg (1.99 mmol, 82.4%) 2′,3′-dideoxyinosine and 51 mg (0.38 mmol, 15.6%) hypoxanthine.

EXAMPLE 9

Production of 2′,3′-dideoxyadenosine

To a solution mixture of 10 ml of acetonitrile and 1 ml of water, 1 g (2.41 mmol) of 9-(2,5-O-diacetyl-3-bromo-3-deoxy-β-D-xylofuranosyl) adenine, 256 mg of 5% palladium carbon containing 50% water, 1.2 ml of 20% sodium carbonate and 435 mg of sodium acetate were added. While blowing hydrogen thereinto, the mixture was stirred at room temperature for 2 hours.

Reduction was completed in 2 hours. The yield of 5′-O-acetyl-2′,3′-dideoxyadenosine was 73.5% and the molar ratio of the 2′,3′-dideoxy compound to the 3′-deoxy compound was 6.0.

After the filtration of the catalyst, the reaction mixture was concentrated under reduced pressure. The residue was adjusted to pH of 12 with aqueous medium sodium hydroxide, followed by stirring at room temperature for an hour. Then, the pH was adjusted to 8 with hydrochloric acid. The solution was purified using synthetic adsorption resin SP-207 (manufactured by Mitsubishi Chemical Co., Ltd.), then concentrated and cooled to crystallize. After drying, 0.39 mg (1.67 mmol, yield of 69.2%) of 2′,3′-dideoxyadenosine was obtained.

EXAMPLE 10

(1) To a solution of 0.27 ml (4 moles) of acetyl bromide in 2 ml of acetic acid was gradually added 323 mg (1 mmol) of 2′,3′-O-(1-methoxyethylidene) adenosine. After stirring at room temperature for 2 hours, the reaction solution was poured onto saturated sodium hydrogencarbonate aqueous solution followed by extraction with ethyl acetate. As a result of quantitative determination of the organic phase by high performance liquid chromatography (hereafter simply referred to as HPLC), 341 mg (0.824 mmoles) of a mixture of 9-[(3′-bromo-3′-deoxy-2′,5′-di-O-acetyl)-β-D-xylofuranosyl] adenine (hereafter simply referred to as Br-AcO-AR) was produced in a yield of 82%. Further 300 MHz nuclear magnetic resonance absorption spectrum of the isolated product supported the structure of this product.

(2) Br-AcO-AR, 307 mg (0.741 mmoles), and 0.18 ml of triethylamine were dissolved in 30 ml of methanol and 620 mg of 2% palladium carbon was added to the solution. While stirring the mixture at room temperature, hydrogen gas was passed in a flow rate of 40 ml/min. After the palladium carbon was filtered, the filtrate was washed with ethanol and the solvent was distilled off under reduced pressure. The residue was dissolved in 8 ml of methanol and 0.4 ml of 28% sodium methoxide (methanolic solution) was added to the solution. The mixture was stirred at room temperature for 30 minutes. The reaction solution was quantitatively determined by HPLC, where 77.8 mg (0.33 mmoles) of 2′,3′-dideoxyadenosine and 32.4 mg (0.30 mmoles) of 3′-deoxyadenosine were produced in yields of 45% and 17%, respectively. 300 MHz nuclear magnetic resonance spectra of the purified and isolated 2′,3′-dideoxyadenosine and 3′-deoxyadenosine supported the structures of the products.

EXAMPLE 11

To a liquid obtained by adding 0.4 ml (4.2 moles) of acetic anhydride and 1 ml of 25% hydrobromic acid/acetic acid solution in 1 ml of acetic acid was gradually added 323 mg (1 mmol) of 2′,3′-O-(1-methoxyethylidene) adenosine. After stirring at room temperature for 2 hours, the reaction solution was poured onto saturated sodium hydrogencarbonate aqueous solution followed by extraction with ethyl acetate. As a result of quantitative determination of the organic phase by HPLC, 330 mg (0.80 mmoles) of Br-AcO-AR was produced in a yield of 80%.

EXAMPLE 12

Adenosine, 10 g (37.4 mmoles), was suspended in 70 ml of acetonitrile and 6.73 g (42 mmoles) of trichloroacetic acid and then 6.0 ml (46 mmoles) of trimethyl orthoacetate were added to the suspension. The mixture was stirred with heating at 50° C. for an hour and 40 minutes. After the reaction, the solvent was distilled off under reduced pressure until the volume of the residual liquid became 35 ml. The solution was slowly added to 72 ml of acetic acid containing 12.3 ml of acetyl bromide at 0° C. while stirring. After completion of the addition, the mixture was stirred at 15° to 20° C. for further 50 minutes to finally obtain a homogeneous solution. The solution was neutralized with 20% sodium carbonate aqueous solution followed by extraction with 140 ml of acetonitrile. According to HPLC analysis, the extract contained 12.77 g (yield of 82.1% based on adenosine) of a mixture of 9-((3'-bromo-3'-deoxy-2',5'-di-O-acetyl)-β-D-xylofuranosyl)-adenine and 9-((2'-bromo-2'-deoxy-3',5'-di-O-acetyl)-β-D-arabino-furanosyl) adenine.

EXAMPLE 13

The objective mixture was obtained in a yield of 84.9% based on adenosine by conducting the reaction in a manner similar to Example 2 except that the initial reaction solvent was changed from acetonitrile to trimethyl phosphate.

EXAMPLE 14

(1) Inosine, 10 g (37.2 mmoles), was suspended in 100 ml of DMF and 33.2 ml (260 mmoles) of trimethyl orthoacetate and then 10.64 g (56.0 mmoles) of p-toluenesulfonic acid monohydrate were added to the suspension. The mixture was stirred at 15° to 20° C. for 30 minutes. After the reaction, the reaction mixture was neutralized with 28% methanolic solution of sodium methoxide. The solvent was distilled off under reduced pressure. The residue was suspended in 130 ml of acetonitrile and the suspension was slowly added to 71 ml of acetic acid containing 11.0 ml (149 mmoles) of acetyl bromide at 0° C. while stirring. After completion of the addition, the mixture was stirred at 15° to 20° C. for further 30 minutes. The solution was neutralized with 10% sodium carbonate aqueous solution followed by extraction with 140 ml of acetonitrile. According to HPLC analysis, the extract contained 11.60 g (yield of 75.1% based on inosine) of a mixture of 9-{(3'-bromo-3'-deoxy-2',5'-di-O-acetyl)-β-D xylofuranosyl} hypoxanthine and 9-{(2'-bromo-2'deoxy-3',5'-di-O-acetyl)-β-D-arabinofuranosyl} hypoxanthine (hereafter simply referred to as Br—AcO—HxR). 300 MHz nuclear magnetic resonance absorption spectrum of the isolated product supported the structure of this product.

(2) Br—AcO—HxR, 415 mg (1.0 mmol), was dissolved in 30 ml of methanol containing 0.24 ml of triethylamine and 170 mg of 10% palladium carbon was added to the solution. While stirring the mixture at room temperature, hydrogen gas was passed in a flow rate of 40 ml/min. After the palladium carbon was filtered off, the filtrate was washed with ethanol and the solvent was distilled off under reduced pressure. The residue was dissolved in 8 ml of methanol and 0.54 ml of 28% sodium methoxide (methanolic solution) was added to the solution. The mixture was stirred at room temperature for 30 minutes. The reaction solution was quantitatively determined by HPLC, where 63.7 mg (0.27 mmoles) of 2',3'-dideoxyinosine and 93.2 mg (0.37 mmoles) of 3'-deoxyinosine were produced in yields of 7% and 37%, respectively. 300 MHz nuclear magnetic resonance spectra of the purified and isolated 2',3'-dideoxyinosine and 3'-deoxyinosine supported the structures of the products.

EXAMPLE 15

Uridine, (1.0 g, 10 mmoles), was suspended in acetonitrile (5.0 ml) and trichloroacetic acid (0.737 g, 4.51 mmoles) and then trimethyl orthoacetate (0.63 ml, 4.92 mmoles) were added to the suspension. The mixture was stirred with heating at 15° to 20° C. for an hour. After the reaction, the solvent was distilled off under reduced pressure. The residue was again dissolved in acetonitrile (1.21 ml, 16.4 mmoles). The solution was slowly added to acetic acid containing acetyl bromide (1.21 ml, 16.4 mmoles) under ice cooling while vigorously stirring. After completion of the addition, the mixture was stirred at 15° to 20° C. for further 2 hours. The solution was neutralized with 10% sodium carbonate aqueous solution followed by extraction with 20 ml of ethyl acetate. According to HPLC analysis, the extract contained 0.561 g (yield of 35.0% based on uridine) of 1-{(2'-bromo-2'-deoxy-3',5'-di-O-acetyl) -D-ribofuranosyl}-uracil.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for producing a 2',3'-dideoxynucleoside of the formula

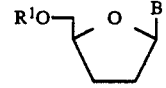

wherein B is adenine, $R^1$ is hydrogen, $C_{1-12}$ acyl, $C_{-1-12}$ alkyl, $C_{7-8}$ aralkyl or silyl, said process comprising:

reducing a nucleoside of the formula IIIa or IIIb

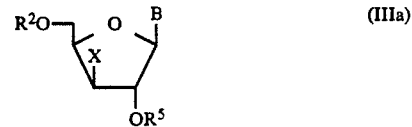

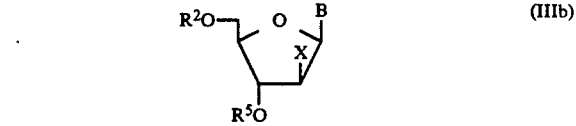

wherein $R^2$ is hydrogen, $C_{1-12}$ acyl, $C_{1-12}$ alkyl, $C_{7-8}$ aralkyl or silyl, X is Cl, Br or I, $R^5$ is $C_{1-12}$ acyl and B is adenine, with hydrogen in an aqueous solvent comprising an aqueous solvent mixture of acetonitrile or ethyl acetate and water, said aqueous solvent containing a base selected from the group consisting of sodium hydroxide/sodium acetate and sodium carbonate/sodium acetate, wherein said solvent has a pH of 9–11 in the presence of a palladium catalyst.

2. The process of claim 1, further comprising reacting a nucleoside of the formula (II)

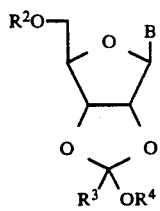

wherein B is adenine, $R^2$ is hydrogen, $C_{1-12}$ acyl, $C_{1-12}$ alkyl, $C_{7-8}$ aralkyl or silyl, $R^3$ is hydrogen, $C_{1-5}$ alkyl or $C_{6-7}$ aryl and $R^4$ is $C_{1-12}$ alkyl, with a $C_{1-12}$ acid halide or a combination of a $C_{2-24}$ organic acid anhydride and a hydrogen halide, to obtain said nucleoside having formula IIIa or IIIb.

3. The process of claim 2, further comprising reacting a nucleoside of formula I

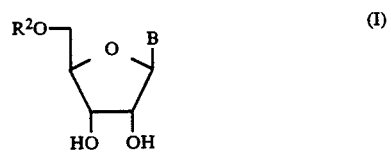

wherein $R^2$ is hydrogen, $C_{1-12}$ acyl, $C_{1-12}$ alkyl, $C_{7-8}$ aralkyl or silyl and B is adenine, with a tri-$(C_{1-12})$-alkyl ortho$(C_{1-8})$-carboxylate reagent in the presence of an organic acid to obtain said nucleoside II which is 1-$(C_{1-12})$-alkoxy-$(C_{1-6})$-alkylidenated or 1-$(C_{1-12})$-alkoxy-$(C_{7-8})$-aralkylidenated at its 2'-position and 3'-position.

4. The process of claim 1, wherein $R^2$ is $C_{1-12}$ acyl.

5. The process of claim 1, wherein $R^2$ is acetyl.

6. The process of claim 1, wherein said base is sodium hydroxide and sodium acetate.

7. The process of claim 3, wherein said organic acid is a $C_{1-6}$ organic acid.

8. The process of claim 7, wherein said organic acid is formic acid or acetic acid.

9. The process of claim 2, wherein said acid halide is an acid chloride, acid bromide or acid iodide.

10. The process of claim 9, wherein said acid halide is a $C_{2-12}$ acyl halide.

11. The process of claim 10, wherein said acyl halide is an acetyl halide or a benzoyl halide.

12. The process of claim 2, wherein said organic acid anhydride is acetic anhydride.

* * * * *